US010517292B2

(12) United States Patent
Guerret et al.

(10) Patent No.: US 10,517,292 B2
(45) Date of Patent: Dec. 31, 2019

(54) OXO-DEGRADABLE PROJECTILES CONTAINING PHEROMONES

(71) Applicant: MELCHIOR MATERIAL AND LIFE SCIENCE FRANCE, Lacq (FR)

(72) Inventors: Olivier Guerret, Pern (FR); Samuel Dufour, Orthez (FR)

(73) Assignee: MELCHIOR MATERIAL AND LIFE SCIENCE FRANCE, Lacq (FR)

( * ) Notice: Subject to any disclaimer, the term of this patent is extended or adjusted under 35 U.S.C. 154(b) by 0 days.

(21) Appl. No.: 15/762,629

(22) PCT Filed: Sep. 23, 2016

(86) PCT No.: PCT/EP2016/072668
§ 371 (c)(1),
(2) Date: Mar. 23, 2018

(87) PCT Pub. No.: WO2017/050956
PCT Pub. Date: Mar. 30, 2017

(65) Prior Publication Data

US 2018/0279607 A1 Oct. 4, 2018

(30) Foreign Application Priority Data

Sep. 25, 2015 (FR) ..................................... 15 59087

(51) Int. Cl.
*A01N 25/34* (2006.01)
*A01N 25/04* (2006.01)
(Continued)

(52) U.S. Cl.
CPC ............... *A01N 25/34* (2013.01); *A01M 1/02* (2013.01); *A01M 29/12* (2013.01); *A01N 25/04* (2013.01);
(Continued)

(58) Field of Classification Search
CPC ........ A01N 25/34; A01N 25/04; A01N 25/18; A01N 63/02; A01N 37/06; A01N 35/02;
(Continued)

(56) References Cited

U.S. PATENT DOCUMENTS

2002/0061325 A1 * 5/2002 Ingram .................. A01N 31/14
424/408

FOREIGN PATENT DOCUMENTS

EP 1 230 855 A1 8/2002
EP 1 652 430 A1 5/2006
(Continued)

OTHER PUBLICATIONS

International Search Report, issued in PCT/EP2016/072668, dated Dec. 12, 2016.
(Continued)

*Primary Examiner* — Carlos A Azpuru
(74) *Attorney, Agent, or Firm* — Birch, Stewart, Kolasch & Birch, LLP

(57) ABSTRACT

The invention relates to paintball-pellet-type projectiles containing insect pheromones encapsulated in an aqueous oil-in-water-type formulation. Said formulations can release said pheromones in a sustained manner. Said projectiles are characterised in that they contain the aqueous formulation of encapsulated pheromone compatible with the envelope of the projectile composed of oxo-degradable polymer. The aim of the invention is to use said projectiles to treat trees against insect pests by spraying and bursting said projectiles on the trunks of said trees.

16 Claims, 2 Drawing Sheets

(51) Int. Cl.

| | |
|---|---|
| ***A01N 25/18*** | (2006.01) |
| ***F42B 12/50*** | (2006.01) |
| ***A01M 29/12*** | (2011.01) |
| ***A01M 1/02*** | (2006.01) |
| ***F42B 6/10*** | (2006.01) |
| ***F42B 12/40*** | (2006.01) |
| *A01N 35/02* | (2006.01) |
| *A01N 37/06* | (2006.01) |
| *A01N 63/02* | (2006.01) |

(52) U.S. Cl.
CPC ................ *A01N 25/18* (2013.01); *F42B 6/10* (2013.01); *F42B 12/40* (2013.01); *F42B 12/50* (2013.01); *A01N 35/02* (2013.01); *A01N 37/06* (2013.01); *A01N 63/02* (2013.01)

(58) Field of Classification Search
CPC . A01M 29/12; A01M 1/02; F42B 6/10; F42B 12/40
See application file for complete search history.

(56) References Cited

FOREIGN PATENT DOCUMENTS

| | | | |
|---|---|---|---|
| WO | WO 2009/090545 | A2 | 7/2009 |
| WO | WO 2012/034167 | A1 | 3/2012 |
| WO | WO 2012/095444 | A2 | 7/2012 |

OTHER PUBLICATIONS

Written Opinion of the International Searching Authority, issued in PCT/EP2016/072668, dated Dec. 12, 2016.

* cited by examiner

OXO-DEGRADABLE PROJECTILES CONTAINING PHEROMONES

INTRODUCTION

The present invention relates to the production and use of paintball type projectiles containing pheromones such as the pheromones of processionary caterpillars, encapsulated in an emulsion type aqueous formulation. Said formulations are capable of releasing said pheromones in a prolonged manner. Said projectiles have the feature of containing an encapsulated aqueous formulation of pheromone compatible with the projectile shell composed of oxo-degradable or oxo-biodegradable polymer. Another object of the invention is the use of these innovative systems for treating forests or orchards against insect pests via the sexual confusion technique.

PRIOR ART

The use of pheromones for controlling insect populations in agriculture or forestry is well-known to those skilled in the art. A pheromone is a chemical substance produced by an animal and which is a stimulus for individuals of the same species or of another species. Pheromones can thus be produced either by living organisms or artificially by chemical synthesis.

The mechanism of action of pheromone-based treatments is either to guide the insects toward an insect trap or to introduce sexual confusion by saturating with pheromones the insects' antennae, which normally enable a male to find females (or vice versa) (Behavior—modifying chemicals for insect management: applications of pheromones and other attractants, Chapter 4 edited by Richard L. Ridgway, Robert M. Silverstein, May N. Inscoe).

In the case of arboriculture, the usual techniques for spreading pheromones are wick bottles, programmable vaporizers, or pheromone-soaked strips suspended from the branches. By way of example, mention may be made of wick bottles such as those sold under the Rhynchotrak® or Rhyncopro® brands, plastics (Cosmotrack®) or gets soaked with the pheromone-containing substance (for example US 20110014257 or U.S. Pat. No. 8,828,374 B2), porous plastic capsules (BASF products for example sold under the Rak® brand) or programmable vaporizer technologies (US 2008/0184614, or the product Checkmate®). Although interesting, these techniques have many drawbacks, including their implementation costs (which includes installing and removing diffusers) and their production costs. Moreover, in the case of forestry, problems related to ease of installation become even more obvious due to tree height and the difficulty of accessing certain locations.

Other techniques have thus been envisaged, such as aerial application of microparticles (U.S. Pat. No. 6,540,991) or the use of projectiles launched into tree branches. The latter techniques are promising but meet objections in terms of respect for the environment.

For example, in 1974, James C. Hale had the idea of using pistol or rifle type projectile launching systems for marking trees (U.S. Pat. No. 3,788,298). Several proposals were then made to adapt that technique for treating forests with pesticides or pheromones against forest pests, with notably the development of various types of projectiles: projectiles connected by a spring as in U.S. Pat. No. 8,561,343, projectile or explosive cartridges having one or two compartments as described in U.S. Pat. No. 6,772,694B1 or US 200606518A1. Indeed, one of the major difficulties in designing projectiles suitable for a launcher such as a compressed-air pistol or rifle is that the "bullets" must be simultaneously sufficiently resistant, chemically compatible with their contents (pheromone or pesticide-based composition), and easily ruptured upon impact. Thus, the projectiles used often consist of a gelatin shell (patent US20020061325 A) which is incompatible with pheromone compositions containing water (problem of the gelatin shell softening in the presence of an aqueous medium, thus making projection of the shell mechanically impossible). Document US20020061325 specifically states that the gelatin shells are intended to contain hydrophobic fill materials due to this incompatibility with water-based or water-containing fill compositions. Storage and transport of gelatin-shell projectiles are thus problematic because they should not be exposed to moisture, which means that they must be stored and transported in heat-sealed airtight packaging. Although many such compositions lend themselves to a paintball type leisure use where the contents of the bag, once opened, are quickly used due to the firing rate, for forest tree marking applications the ambient moisture associated with a much lower rate leads to degradation of the shell due to softening.

However, the advantage of aqueous formulations for gradually releasing pheromones is significant because they are environmentally friendly. If the microparticle matrix is itself biodegradable, the whole system (shell and aqueous formulation) is itself biodegradable, which makes it suited to use in the natural environment. In addition, if a solvent other than water was used, its evaporation into the air would lead to atmospheric pollution unsuited to the intensive treatment of forests infested by defoliating insects, for example.

Certain biodegradable shells have been studied in the past. For example, keratin has been proposed to form the shell of projectiles containing a disinfectant in the case of the pine processionary (patent WO 2008/065218). However, apart from the fact that no example of aqueous content is provided, recent work (in particular that of the INRA), shows that keratin is difficult to transform for the industrial production of projectiles that could be filled with an aqueous formulation of pheromone.

In addition, in patent FR 200951799, D. Delhaye describes a paintball system characterized in that the paintball shells are composed of an oxo-biodegradable polymer. That material is a polymer containing transition metals which, under the joint action of oxygen from the air and UV radiation, will degrade the polymer into micro-sized pieces which, in the case of polyolefins, will become biodegradable. Such shells are designed to convey fertilizers and insecticidal or plant protection products which are in liquid form and compatible with the shell material.

The existing solutions are unsatisfactory for dispersing pheromones incompatible with oxo-degradable materials. Moreover, a liquid formulation leads to spatter upon impact and bursting and a significant loss of active material. The inventors have therefore designed aqueous formulations of pheromones which are compatible with oxo-biodegradable polymer projectile shells and which release insect pheromones for several months, making it possible to induce sexual confusion in forest or orchard insect pests.

DESCRIPTION OF THE INVENTION

The applicant has thus developed a new type of projectile, represented in FIG. 1, which is capable of treating trees against insect invasions Thus, in a first embodiment, the present invention concerns a projectile comprising a shell and a fill material characterized in that the shell comprises an oxo-degradable thermoplastic polymer or copolymer and in that the fill material consists of an aqueous formulation of "oil-in-water" emulsion type wherein the aqueous phase comprises a gelling agent and the oil phase comprises a matrix consisting of a mixture of oil and/or wax and pheromone.

In a second embodiment, the projectile according to the invention is characterized in that the oxo-degradable thermoplastic polymer or copolymer of the shell is selected from the group consisting of oxo-degradable polyolefins.

Preferentially, the oxo-degradable thermoplastic polymer or copolymer is selected from the group consisting of oxo-degradable polyethylene and oxo-degradable polypropylene.

In another embodiment of the present invention, the projectile is characterized in that the emulsion of the aqueous formulation comprises 20 to 70 wt. % aqueous phase and 80 to 30% oil phase.

The projectile according to the invention, in another embodiment of the invention, is characterized in that the gelling agent is selected from the group consisting of cellulose ethers, polyurethanes and copolymers of (meth) acrylic acid and ethyl acrylate.

Particularly, the projectile according to the invention is characterized in that the gelling agent is a copolymer of (meth)acrylic acid and ethyl acrylate comprising:

30 to 40 wt. % methacrylic acid 45 to 60 wt. % ethyl acrylate 5 to 20 wt. % macromonomer of general formula (I):

(I)

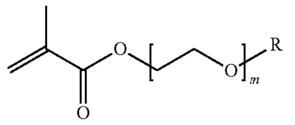

where m is an integer from 1 to 40, preferably from 10 to 30, and where R is a group of general formula $C_nH_{2n+1}$ wherein n is an integer from 9 to 25, preferably from 10 to 20, and more preferentially equal to 12; the pH of the aqueous phase is from 5 to 8.

In a particular embodiment of the invention, the projectile according to the invention is characterized in that the oil phase comprises from 0 to 90 wt. % wax, particularly from 10 to 80 wt. % wax, from 0.1 to 25 wt. % pheromone and from 0 to 90 wt. % oil, particularly from 10 to 80 wt. % oil and 0 to 0.8 wt. % stabilizer, antioxidant and anti-UV.

According to another embodiment of the invention, the pheromone of the projectile is selected from the group of fatty-chain pheromones of insects, in particular a sex pheromone of pine processionary moths, oak processionary moths, box tree moths, silk moths and codling moths.

It is also another object of the present invention to provide a projectile as defined above, characterized in that the weight ratio of shell to fill material is 1:20 to 1:200.

Also, in an embodiment of the invention, the projectile is characterized in that the thickness of the shell is 50 to 500 μm, preferentially 80 to 250 μm.

In a particular embodiment of the invention, the projectile is characterized in that it is a sphere having a diameter of 0.5 to 5 cm, preferably of 1 to 3 cm.

In order to ensure satisfactory spreading upon impact, the projectile according to one of the variants of the invention is characterized in that the viscosity of the aqueous formulation of fill material is from 1000 to 15000 centipoises at 25° C., particularly from 2000 to 10000 centipoises at 25° C.

In another embodiment, the projectile according to the invention is characterized in that the weight ratio of oil and/or wax to pheromone in the oil phase is from 70:30 to 99.5:0.5, more particularly from 80:20 to 98:2.

The present invention also concerns the use of a projectile according to one of the embodiments described herein for protecting a stand of trees against an insect pest characterized by the fact that the projectile is projected and bursts on the trunk of the trees of the stand to be protected. In particular, the projectile is projected with sufficient force to cause the shell to burst and to cause all or part of the fill material to adhere to the trunk.

The use of a projectile according to the invention as described is also characterized in that the insect pest is selected from the group consisting of the pine processionary moth, the oak processionary moth, the box tree moth, the silk moth and the codling moth.

Lastly, in a particular embodiment of the invention, the use of the projectile as described is characterized in that said projectile is projected and bursts at the canopy level.

Thus, the projectile according to the invention comprises a shell and a fill material and is characterized in that the shell comprises an oxo-degradable thermoplastic polymer or copolymer and the fill material comprises an aqueous formulation of "oil-in-water" emulsion type wherein the aqueous phase comprises a gelling agent and the oil phase comprises a matrix consisting of a mixture of oil and/or wax and pheromone.

The aqueous formulation of the projectile is capable of slowly releasing pheromones and resisting washing-off due to the elements, in order to control the behavior of insects or animals.

The projectile can have a spherical, ovoid, cylindrical or conical shape or any other molded shape. Preferably the projectile is a sphere having a diameter of 0.5 to 5 cm, particularly of 1 to 3 cm in diameter.

The projectile shell consists of an oxo-degradable or oxo-biodegradable thermoplastic polymer or copolymer, preferably oxo-degradable or oxo-biodegradable polyethylene or polypropylene.

The expression "thermoplastic" refers to a material that softens repeatedly when heated above a certain temperature, but that hardens again below that temperature. Such a material will thus always reversibly retain its initial thermoplasticity.

The expression "oxo-degradable" or "oxo-biodegradable" refers to a polymeric material that can degrade biologically in nature, after having first undergone abiotic oxidative degradation under the combined effects of heat and UV, by oxidation of carbon-hydrogen bonds, which lowers the material's molecular weight. The material oxidized in the presence of microorganisms is then converted to $CO_2$, water and non-sterile biomass, without generating toxic residues.

The fill material of the projectiles according to the invention comprises, or consists of, an aqueous formulation which slowly releases the pheromones. Said aqueous formulation comprises, or consists of, an oil-in-water type emulsion which comprises from 20 to 70 wt. % aqueous phase and 80 to 30 wt. % dispersed oil phase comprising, or consisting of, a matrix based on biodegradable natural wax and/or natural oil in which are incorporated the pheromones for controlling insect behavior.

The stability of the emulsion of the aqueous phase is provided by the presence of a water-soluble gelling agent or rheology modifier. The gelling agent, or rheology modifier, helps to increase the viscosity of the aqueous phase of fill material so that the latter does not scatter when the projectile bursts upon impact. The nature of the water-soluble gelling agent is not critical insofar as it is compatible with the desired viscosity and the pheromone contained in the oil phase. The water-soluble gelling agent or rheology modifier may be selected from polysaccharides or from the group consisting of cellulose ethers, polyurethanes, and HASE type copolymers.

Examples of cellulose ether include methyl cellulose, hydroxymethyl cellulose, hydroxyethylcellutose, hydroxypropylcellulose, hydroxyethyl methyl cellulose, hydroxypropyt methyl cellulose and carboxymethylcellulose.

It should be recalled that hydrophobically modified alkali-swellable emulsion (HASE) type polymers are copolymers of (meth)acrylic acid and alkyl acrylate produced by radical polymerization in emulsion and which have the property when neutralized by a base such as soda or ammonia to become water-soluble and to modify the rheology of the water, but whose composition further comprises hydrophobic macromonomers of general formula:

(I)

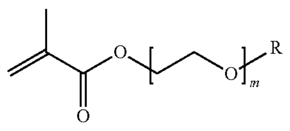

Where m is an integer from 1 to 40, in general greater than 5, and where R is a group of general formula $C_nH_{2n+1}$ wherein n is an integer from 10 to 30, particularly from 9 to 25, more preferably from 10 to 20. They also have the capacity to modify the rheology of the aqueous solution.

They are prepared according to methods well-known to those skilled in the art by means of a mercaptan type chain-transfer agent.

The amount of water-soluble gelling agent in the aqueous phase can be from 5 wt. % to 20 wt. %. Particularly, from 5 to 10 wt. % of the aqueous phase. The amount of said water-soluble gelling agent can be adjusted as a function of its nature and gelling power, and this in order to obtain the desired viscosity for the aqueous formulation of fill material of the projectiles according to the invention.

Preferentially, the gelling agent is an acrylic copolymer, in particular a HASE type acrylic copolymer, and is characterized in that it contains:

30 to 40 wt. % methacrylic acid, 45 to 60 wt. % ethyl acrylate,

5% to 20 wt. % macromonomer of general formula (I):

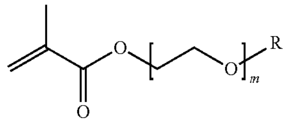

Where m is an integer from 1 to 40, preferably from 10 to 30, and where R a group of general formula $C_nH_{2n+1}$ wherein n is an integer from 9 to 25, preferably from 10 to 20, and more preferentially equal to 12.

If an acrylic copolymer, in particular a HASE type acrylic copolymer as defined above, is used as water-soluble gelling agent, the amount thereof in the aqueous phase can be from 5 to 15 wt. %, more particularly from 5 to 10 wt. %. In order to obtain the desired viscosity, the pH of the aqueous phase will be from 5 to 8, particularly from 6 to 8, in order to ensure the gelation of said copolymer and to reach the desired viscosity.

The dispersed oil phase of the emulsion comprised in the aqueous formulation of fill material of the projectiles according to the invention comprises from 10 to 90 wt. % wax, particularly from 60 to 80 wt. % wax, 10 to 90 wt. % oil, particularly 8 to 35 wt. % oil, 0.1 to 25 wt. % pheromone, particularly from 0.5 to 20 wt. % pheromone, and from 0 to 0.8 wt. %, particularly from 0.1 to 0.5 wt. % stabilizer.

For the purposes of the invention, the term "wax" means a lipophilic compound which is solid at room temperature (about 25° C.) and atmospheric pressure (760 mmHg). The waxes that can be used in a composition according to the invention may be selected from waxes of animal, vegetable, mineral or synthetic origin and mixtures thereof. In particular, use can be made of hydrocarbon waxes such as beeswax, lanolin wax and Chinese insect waxes; rice wax, carnauba wax, candelilla wax, jojoba wax, ouricury wax, esparto wax, cork fiber wax, sugar cane wax, Japanese wax and sumac wax, montan wax, microcrystalline waxes, paraffins and ozocerite; polyethylene waxes, waxes obtained by Fischer-Tropsch synthesis and waxy copolymers and esters thereof. Mention may also be made of waxes obtained by catalytic hydrogenation of animal or vegetable oils having linear or branched $C_8$-$C_{32}$ fatty chains. Among those, particular mention may be made of hydrogenated jojoba oil, hydrogenated sunflower oil, hydrogenated castor oil, hydrogenated copra oil and hydrogenated lanolin oil, di-(trimethylol-1,1,1 propane) tetrastearate. Use may also be made of waxes obtained by transesterification and hydrogenation of vegetable oils, such as castor oil or olive oil, such as the waxes sold under the names Phytowax ricin 16L64® and 22L73® and Phytowax Olive 18L57 by the company SOPHIM.

For the purposes of the invention, the term "oil" means a water-immiscible nonaqueous compound which is liquid at room temperature (about 25° C.) and atmospheric pressure (760 mmHg). The oil according to the invention can be selected from vegetable oils. Particularly, the oil according to the invention will be selected from the group consisting of sunflower oil, peanut oil, soybean oil, rapeseed oil, corn oil, olive oil, grape oil, walnut oil, linseed oil, palm oil, coconut oil, argan oil, avocado oil, almond oil, hazel nut oil, pistachio oil, rice oil, cotton seed oil, wheat germ oil, sesame oil, or mixtures thereof. Preferably, the oil is selected as a function of the crop sought to be protected from insect pests, in particular lepidopterans.

A stabilizer, or a mixture of stabilizers, antioxidant and/or anti UV, can be contained in the fill material of the projectiles according to the invention in order to protect the components of the oil phase, in particular the pheromones, from oxidation and/or UV. The stabilizer can be selected from the group consisting of n-butyl-4-hydroxybenzoate (BHB), tocopherol, ter-butyl-hydroquinone (TBH), n-propyl-gallate (PG), t-butyl-hydroxyanisole (BHA), methyl para-hydroxybenzoate (MHB), N,N diethyltoluamide (DT), t-butyl-5 hydroxytoluene (BHT) and α-thioglycerin (TG), nitroxides and alkoxyamines and mixtures thereof. The one or more stabilizers protect the oil, the wax and/or the pheromone from oxidation and/or UV.

The one or more pheromones contained in the projectiles according to the invention are particularly pheromones of insects, more particularly fatty-chain pheromones of insects. More particularly, the one or more pheromones are fatty-chain pheromones of lepidopterans. Particularly, the projectiles according to the invention contain sex pheromones of lepidopterans. The sex pheromones of insects such as lepidopterans are characterized in that they are composed of mixtures of unsaturated alcohol-, ester- or aldehyde-terminated fatty-chain molecules.

As pheromone contained in the projectiles according to the invention, mention may be made of the pheromones of box tree moths and codling moths, pests to trees such as boxwood, chestnut, walnut, apple, pear. More particularly, the pheromone can be a sex pheromone of pine and oak processionary moths. Known for their method of travel in nose-to-tail columns, the larvae nest in the needles of various pine species or in the leaves of oaks, causing significant weakening of the trees. A common characteristic of these pests is that the moths travel in the tree canopy, and it is one of the advantages of the invention to be able to place pheromone diffusion points in the trees at heights up to several meters without needing to transport heavy equipment such as ladders or boom lifts.

The shell of the projectiles according to the present invention provides mechanical resistance during storage, handling and projection, for example using a paintball type air gun, and also allows, by rupturing upon impact on a hard substrate such as the trunk of a tree, the projectile to burst and to release the fill material. The weight ratio between the shell and the fill material can be selected in order to promote either mechanical resistance or ease of bursting upon impact, and this according to the size of the projectile, the nature of the shell material and the nature of the fill formulation. In this context, the nature of the constituent material of the shell and the dimensional features thereof, as well as the viscosity of the fill material, are such that the impact of a projectile on a hard surface causes the shell to burst and the fill formulation to spread while avoiding spatter. Particularly, the weight ratio of shell to fill material can be 1:20 to 1:200.

The thickness of the shell of the projectiles according to the invention will depend on the size of the projectile, the weight ratio of shell to fill material, the viscosity of said fill material, and also the nature of the oxo-degradable thermoplastic material.

The thickness of the shell can thus be from 50 to 500 μm, particularly from 80 to 250 μm, more particularly from 100 to 200 μm, for example. By way of example, for a spherical projectile whose shell material is an oxo-degradable thermoplastic polymer or copolymer such as oxo-degradable polypropylene, having a size of about 1.75 cm in diameter, the thickness of the shell is of the order of 120 μm.

Typically, a process for producing the projectiles according to the invention corresponds to that described in WO2014016510 and comprises the following steps: receipt of two sheets of oxo-degradable thermoplastic film, each sheet comprising at least one column of shaped cavities; movement of the two sheets to align the respective cavities of each sheet and gapping of the sheets via pairs of bars which successively clamp the sheets on each side of the pairs of columns of cavities, filling of the pocket delimited between the two pairs of bars with the fill formulation to fill the cavities and welding of the sheets around the cavities to form the projectiles.

In addition to its role as stabilizer, the gelling agent, or rheology modifier, controls the viscosity of the fill formulation. During production of the projectiles, the aqueous formulation of fill material must be sufficiently liquid to allow filling of the projectiles at high rates. Upon impact on a trunk, it must be sufficiently viscous to ensure the formation of a film of adequate thickness.

The viscosity of the aqueous formulation of fill material of the projectile according to the invention is selected so as to be sufficiently low to allow easy filling of the cavities of the projectiles during production thereof but sufficiently high in order to limit spatter when the projectile bursts upon impact on a hard surface, in particular a trunk. The gelling agent and the amounts of said agent, as well as the conditions suited to the nature of said agent, can be used to determine the viscosity of the aqueous formulation of fill material. Thus, when HASE type copolymers and polymers are used, the gelation thereof being determined by pH, the pH of the aqueous phase will be from 5 to 8, particularly from 6 to 8, in order to gel said polymer. Indeed, as the projectiles according to the present invention are particularly intended for applying a pheromonal composition on the trunks of trees, if the viscosity of the fill formulation is too low, spatter is generated when the projectile bursts upon impact, and a significant portion of said formulation is likely to be lost and fall to the ground.

The Brookfield viscosity of the aqueous formulation of fill material is thus from about 1000 to about 15000 centipoises, at 25° C., particularly 2000 to 12000 centipoises, at 25° C., more particularly 2500 to 10000 centipoises, at 25° C. The Brookfield viscosity of the aqueous formulation of fill material can be measured using a Brookfield viscometer, which consists in the application of a moving force to a substance—the aqueous formulation—while rotating at fixed speed a spindle of fixed size immersed in said substance. The substance's resistance to the rotational movement of the spindle is recorded using an internal spiral spring, then converted to viscosimetric units, for example centipoises. By way of illustration, the viscosity of the aqueous formulation of fill material of the projectiles according to the present invention can be in a range corresponding to that going from liquid honey to crystallized honey, mayonnaise or chocolate spread, for example.

The adjustment of the ratio of wax and/or oil to pheromone in the matrix of the oil phase of the emulsion of the aqueous formulation of fill material depends on the solubility of the pheromones in the oil+wax mixture. Said ratio can vary from 70:30 to 99.5:0.5, more particularly from 80:20 to 98:2, even more particularly around 75:25, for example. The projectiles according to the invention are projected against the tree trunks by means of a compressed-air system. The bursting of the projectile causes the spreading of the aqueous formulation, which forms a film on the trunk surface. Slow release of the pheromone through the film thus formed then controls the insects' behavior.

Preferably, the insects targeted by this technology are forest or orchard pests such as the pine processionary or oak processionary, the box tree moth or silk moths, codling moths (of apple, pear, chestnut, walnut trees, etc.). Projection of the projectiles according to the invention makes it possible to create within a forest or wooded area as many pheromone diffusion points as impacts made. A high density of impacts, combined with the controlled release of the pheromone by each diffuser, creates a pheromone cloud that prevents the insect's reproduction cycle from occurring properly. This disturbance reduces the pest population and thus protects the trees from the damage cause thereby. The impacts will be located preferentially at the canopy level and their number will be from 100 to 1000 per hectare.

The advantage of the technique developed in the present invention is to allow the treatment of large woodland areas at a controlled cost, alt while using only biodegradable components containing no organic volatile other than the pheromone itself.

EXAMPLES

Materials:

The pheromones used in forestry are either purchased from industrial manufacturers or manufactured by M2i Development (Lacq, France) according to known processes. In the case of the products synthesized by M2i Development, their characterizations are validated by a comparative analysis with a referent sample using gas chromatography.

Example 1 (not According to the Invention): Incompatibility of the Pure Pheromone in Direct Contact with Oxo-biodegradable Materials The sex pheromone of the box tree moth is the mixture of Z and E-11 hexadecenal in a 5:1 ratio.

A paintball projectile shell consisting of an oxo-biodegradable polyolefin is cut into small pieces of the order of 2 to 5 $mm^2$. The pieces thus obtained are placed in a reactor containing a magnetic stirrer. The reactor is placed under nitrogen.

100 mg of the hexadecenal mixture described above is added to the pieces and stirring is maintained until the liquid has been completely absorbed by the pieces.

Figure 1:
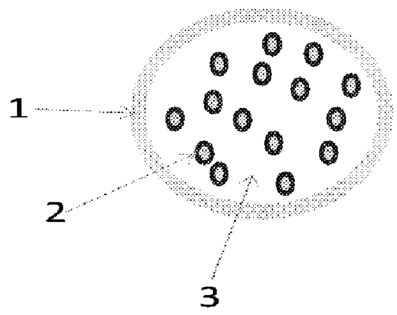
FIG. 1 represents a schematic view of a projectile according to the invention in which (1) represents the projectile shell made of oxo-biodegradable thermoplastic material, (2) represents the particles containing a mixture of pheromone in a matrix based on wax and/or oil and (3) represents the aqueous phase containing the gelling agent, or rheology modifier.
Figure 2:
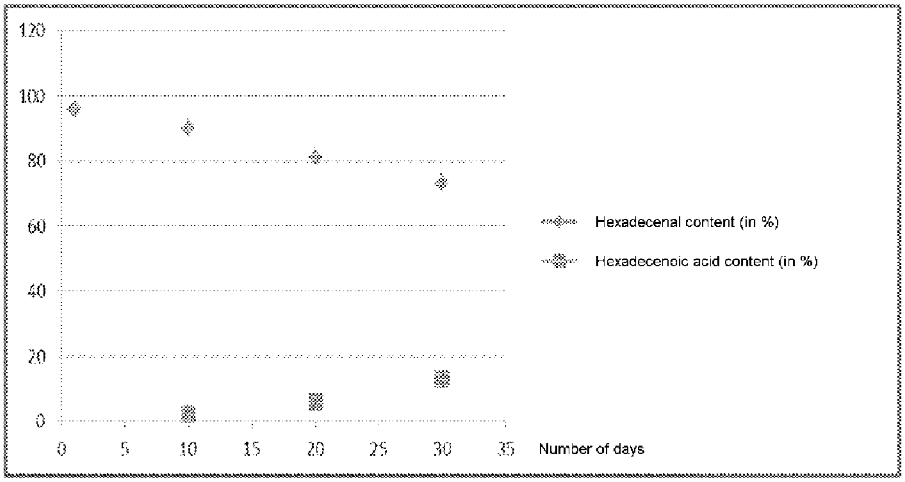
FIG. 2 represents the demonstration of the degradation of the box tree moth pheromone in the presence of an oxo-biodegradable polymer.

The pieces are then separated in two portions:

The first half is stored in an aluminum foil pouch, under nitrogen (control). The second half is placed in a closed transparent cup under air in the light. Pieces are regularly analyzed by gas chromatography. Changes in the pheromonal mixture are reported in the following graph (FIG. 2):

FIG. 2 shows that the oxo-biodegradable polyolefin decomposes the pheromone mixture in the presence of oxygen when the latter is in direct contact with the polyolefin. One notes, among other things, the appearance of hexadecenoic acid produced by oxidation of the pheromone. This example illustrates the problem of the compatibility of the pheromones with the oxo-biodegradable polymers and the importance of protecting the pheromone in an emulsion as illustrated in the present invention.

Example 2: Production of Aqueous Formulations Containing Pheromones

The acrylic rheology modifiers used in the formulations are HASE type acrylic copolymers provided by the company Coatex (Rheotech® range; France).

The HASE 1 copolymer used for the exemplifications consists of:

35.5 wt. % methacrylic acid, 52.4 wt. % ethyl acrylate, 12 wt. % macromonomer of formula (I) wherein m=30 and n=12.

General Protocol for Producing Aqueous Formulation Containing Pheromones:

Components of the formulation:

| | |
|---|---|
| Aqueous phase: | HASE1 rheology modifier |
| | $H_2O$ |
| | 10% NaOH |
| Solution 1 | Wax/oil |
| | Pheromone |
| | Stabilizer (BHT) |
| Solution 2 | $H_3PO_4$ (4%) |

Procedure:

Solution 1 is prepared by melting the beeswax, sunflower oil, pheromone and stabilizer (BHT) mixture at 70° C. in a 4-L jacketed reactor equipped with mechanical stirring (IKA) and a standard anchor or impeller type stirring rod. The internal temperature of the reactor must be higher than the melting point of wax.

In a second jacketed reactor (20 L) equipped with mechanical stirring (IKA) and a standard anchor or impeller type stirring rod, under stirring, the aqueous phase is prepared by loading water, soda and the rheological additive. This mixture is heated to a temperature higher than the melting point of wax.

When solution 1 is molten, it is added dropwise to the aqueous phase using a Watson-Marlow pump (rotational speed 200) over about 5'.

In order to adjust the viscosity of the prepared formulation, solution 2 (phosphoric acid) is finally added dropwise over 15' with a jacket temperature of 35° C. The medium is stirred for 5' before being cooled and returned to room temperature Controlled-release Aqueous Formulation for the Pine Processionary The aqueous formulation of the pine processionary pheromone was prepared according to the general procedure above with the amounts of reagents presented below.

| Test | 1 |
|---|---|
| Aqueous phase | |
| HASE 1 rheology modifier | 1.88 g |
| $H_2O$ | 15.48 g |
| NaOH (10%) | 0.73 g |
| Solution 1 | |
| Beeswax | 3.84 g |
| Sunflower oil | 11 g |
| Pine processionary pheromone | 0.46 g |
| Stabilizer (BHT) | 0.46 g |
| Solution 2 | |
| $H_3PO_4$ (4%) | 3.22 g |

Example 3: Production of Projectiles According to the Invention Starting with the Formulations of Example 2

The paintball type projectiles according to the invention were produced by the company Polytek according to the process described in patent WO 2014016510 A1 and in the present description. The material used is an oxo-biodegradable polypropylene. The process comprises providing two films of similar polymeric material (oxo-biodegradable polypropylene). The fill composition as described above is provided. The films are arranged in an encapsulation unit comprising two molding drums, each comprising a cylinder wherein a plurality of hemispherical cavities is formed, said drums being arranged such that axes thereof are parallel and the cylinders are joined, said films feeding continuously in the encapsulation unit so as to arrive tangentially on said cylinders. The films are transformed into capsule portions having a substantially hemispherical shape by means of counter-rotating rotation of the molding drum cylinders. The fill composition is introduced into said capsule portions which are joined and closed to form shells filled with the pheromonal composition. The diameter of the substantially spherical projectiles obtained is 1.75 cm (68 caliber).

Example 4: Projection of the Projectiles of Example 3 onto Trees

The transfer of material is measured on 10 trunks according to the following protocol:

After 24 h (the time necessary for the water to evaporate), the trunks are scraped to recover the dry deposit and then each sample is dissolved in hot heptane and filtered so as to eliminate solid particles from the trunk or shell residues. The heptane is evaporated under reduced pressure and then the residue, which corresponds to the amount of material transferred during impact, is weighed. This weight is then compared to the theoretical weight of the matrix and pheromone contained in each projectile (1.01 g).

The results are as follows:

| | Trunk | | | | | | | | | |
|---|---|---|---|---|---|---|---|---|---|---|
| | 1 | 2 | 3 | 4 | 5 | 6 | 7 | 8 | 9 | 10 |
| % transfer | 85 | 86 | 90 | 88 | 91 | 86 | 93 | 90 | 85 | 88 |

Which is on average 88.2% transfer. This shows that the fill material of the projectiles according to the invention is nearly completely retained on the substrate and that very little loss was sustained when the projectiles burst upon impact on the trunks.

Example 5: Test of Sexual Confusion in a Maritime Pine Stand 500 projectiles containing 1.01 g of oil/wax formulation with a 10% load of (Z)-13-hexadecen-11-yn-1-ol acetate, a sexual attraction pheromone of the pine processionary moth, dispersed in 1.2 g of water and containing 3 wt. % HASE 1, were prepared according to example 3.

Figure 3:
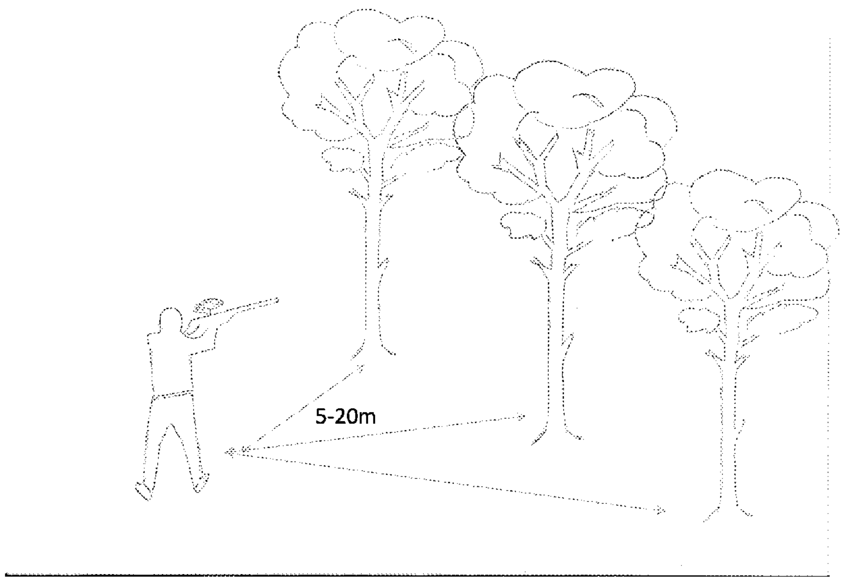
FIG. 3 represents an example of projection of the projectiles onto pines, illustrating the advantage of the system making it possible to place several diffusers effortlessly.

The 500 projectiles were shot at the pines of a 5-ha stand at a rate of 100 projectiles per hectare and at a height of 2.5 m to 5 m. The shooting grid tends to follow one shot every 10 m as a function of tree density (FIG. 3).

To monitor population changes on-site, Mastrap L@ type pheromone traps were placed every 10 m in the middle of the stand. Another 10 traps were distributed at the periphery of the stand (25 m therefrom). The results are as follows:

TABLE 2

| number of captures for the 10 traps of each type (these numbers indicate the number of new captures) | | |
|---|---|---|
| | Inner traps | Outer traps |
| T0 + 1 month | 9 | 135 |
| T0 + 2 months | 11 | 154 |
| T0 + 3 months | 14 | 122 |

This example shows the efficacy of the sexual confusion-based protection system according to the invention in protecting against the pine processionary moth.

Furthermore, several rainstorms fell on the stand during the test, which validates the resistance of the films deposited on the trunks during the treatment period.

The invention claimed is:

1. A projectile comprising a shell and a fill material wherein the shell comprises an oxo-degradable thermoplastic polymer or copolymer which is selected from the group consisting of oxo-degradable polyefins, and in that the fill material consists of an aqueous formulation of "oil-in-water" emulsion type wherein the aqueous phase comprises a gelling agent and the oil phase comprises a matrix consisting of a mixture of oil and/or wax and pheromone.

2. The projectile according to claim 1, wherein the oxo-degradable thermoplastic polymer or copolymer is selected from the group consisting of oxo-degradable polyethylene and oxo-degradable polypropylene.

3. The projectile according to claim 1, wherein the emulsion of the aqueous formulation comprises 20 to 70 wt. % aqueous phase and 80 to 30% oil phase.

4. The projectile according to claim 1, wherein the gelling agent is selected from the group consisting of cellulose ethers, polyurethanes and copolymers of (meth)acrylic acid and ethyl acrylate.

5. The projectile according to claim 1, wherein the gelling agent is a copolymer of (meth)acrylic acid and ethyl acrylate comprising:

30 to 40 wt. % methacrylic acid 45 to 60 wt. % ethyl acrylate 5 to 20 wt. % macromonomer of general formula (I):

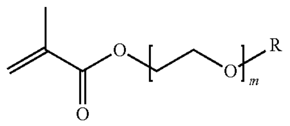

where m is an integer from 1 to 40, preferably from 10 to 30, and where R is a group of general formula CnH2n+1 wherein n is an integer from 9 to 25, preferably from 10 to 20, and more preferentially equal to 12; the pH of the aqueous phase is from 5 to 8.

6. The projectile according to claim 1, wherein the oil phase comprises from 0 to 90 wt. % wax, particularly from 10 to 80 wt. % wax, from 0.1 to 25 wt. % pheromone and from 0 to 90 wt. % oil, particularly from 10 to 80 wt. % oil and 0 to 0.8 wt. % stabilizer.

7. The projectile according to claim 1, wherein the pheromone is selected from the group of fatty-chain pheromones of insects, in particular a sex pheromone of pine processionary moths, oak processionary moths, box tree moths, silk moths and codling moths.

8. The projectile according to claim 1, wherein the weight ratio of shell to fill material is 1:20 to 1:200.

9. The projectile according to claim 1, wherein the thickness of the shell is 50 to 500 μm, preferentially 80 to 250 μm.

10. The projectile according to claim 1, wherein said projectile is a sphere having a diameter of 0.5 to 5 cm, preferably of 1 to 3 cm.

11. The projectile according to claim 1, wherein the viscosity of the aqueous formulation of fill material is from 1000 to 15000 centipoises at 25° C., particularly from 2000 to 10000 centipoises at 25° C.

12. The projectile according to claim 1, wherein the weight ratio of oil and/or wax to pheromone in the oil phase is from 70:30 to 99.5:0.5, more particularly from 80:20 to 98:2.

13. A method for protecting a stand of trees against an insect pest wherein a projectile according to claim 1 is projected and bursts on the trunk of the trees of the stand to be protected.

14. The method according to claim 13, wherein the projectile is projected with sufficient force to cause the shell to burst and to cause all or part of the fill material to adhere to the trunk.

15. The method according to claim 13, wherein the insect pest is selected from the group consisting of the pine processionary moth, the oak processionary moth, the box tree moth, the silk moths and the codling moths.

16. The method according to claim 13, wherein the projectile is projected and bursts at the canopy level.

* * * * *